United States Patent
Moretta et al.

(10) Patent No.: US 7,279,291 B2
(45) Date of Patent: Oct. 9, 2007

(54) POLYPEPTIDES HAVING A TRIGGERING NK ACTIVITY AND BIOLOGICAL APPLICATIONS

(75) Inventors: Alessandro Moretta, Genoa (IT); Cristina Bottino, Genoa (IT); Roberto Biassoni, Genoa (IT)

(73) Assignees: Innate Pharma, S.A., Marseille (FR); Universita Di Genova, Genova (IT)

( * ) Notice: Subject to any disclaimer, the term of this patent is extended or adjusted under 35 U.S.C. 154(b) by 0 days.

(21) Appl. No.: 11/483,991

(22) Filed: Jul. 10, 2006

(65) Prior Publication Data

US 2006/0246068 A1    Nov. 2, 2006

Related U.S. Application Data

(62) Division of application No. 10/451,843, filed as application No. PCT/EP01/15424 on Dec. 27, 2001, now Pat. No. 7,074,409.

(30) Foreign Application Priority Data

Dec. 27, 2000  (EP)  ................. 00403689

(51) Int. Cl.
  *G01N 33/537*  (2006.01)
  *C07K 16/28*   (2006.01)
(52) U.S. Cl. .............. 435/7.1; 435/7.24; 530/350; 530/387.1; 530/388.22
(58) Field of Classification Search .............. None
  See application file for complete search history.

(56) References Cited

OTHER PUBLICATIONS

Vitale Massimo et al. "Identification of NKp80, a Novel Triggering Molecule Expressed by Human NK Cells" *European Journal of Immunology*, Jan. 2001, pp. 233-242, vol. 31, No. 1.
Roda-Navarro et al. "Human KLRFI, a Novel Member of the Killer Cell Lectin-Like Receptor Gene Family: Molecular Characterization, Genomic Structure, Physical Mapping to the NK Gene Complex and Expression Analysis" *European Journal of Immunology*, Feb. 2000, pp. 568-576, vol. 30, No. 2, XP001062417.
Database EMBL 'Online!, HS1225660 Ac No. AA424848, May 24, 1997, Hillier et al. "zw03b04.s1 Soares_NhHMPu_S1 *Homo sapiens* cDNA Clone Image: 768175", XP002192078.
Database EMBL 'Online!, HS16432 Ac No. T60164, Mar. 4, 1995, Hillier et al. "yc22d06.s1 Stratagene Lung (#937210) *Homo sapiens* cDNA Clone Image: 81419", XP002192079.
Moretta et al. "Natural Cytotoxicity Receptors That Trigger Human NK-Cell-Mediated Cytolysis" *Immunology Today*, May 2000, pp. 228-234, vol. 21, No. 5, Elsevier Publications, Cambridge, GB.

*Primary Examiner*—Christina Chan
*Assistant Examiner*—Phuong Huynh
(74) *Attorney, Agent, or Firm*—Saliwanchik, Lloyd & Saliwanchik (57) ABSTRACT

The invention relates to polypeptides having a triggering NK activity and an amino acid sequence that is at least 80% identical over its entire length to the polypeptide having SEQ ID NO: 1, and any immunogenic fragments thereof, as well as to the polyclonal and monoclonal antibodies directed against said polypeptides, and immuno-reactive fragments thereof. Application for detecting NK cells in a sample, for their removal from a sample or for enrichment of NK cells, and for NK cell natural cytotoxicity regulation.

5 Claims, 7 Drawing Sheets

MA152　　　　　　LAP 171

FIGURE 7

POLYPEPTIDES HAVING A TRIGGERING NK ACTIVITY AND BIOLOGICAL APPLICATIONS

CROSS-REFERENCE TO RELATED APPLICATIONS

This application is a divisional of U.S. application Ser. No. 10/451,843, filed Aug. 27, 2003, now U.S. Pat. No. 7,074,409, which is the U.S. national stage application of International Patent Application No. PCT/EP01/15424, filed Dec. 27, 2001.

The invention relates to polypeptides having a triggering NK activity. It also concerns the antibodies raised against said polypeptides and the biological applications of said both polypeptides and antibodies.

NK cells represent an efficient effector mechanism employed by the immune system to rapidly detect and destroy HLA Class I-deficient target cells including tumor and virally infected cells. NK cells are also capable of killing normal allogeneic PHA-induced T cell blasts thus implying that the ligands recognized by the receptors involved in NK cell triggering are not confined to abnormal cells. On the other hand, killing of autologous PHA blasts can be induced in the presence of appropriate anti-HLA class I mAbs capable of disrupting the interaction between HLA Class I molecules and the inhibitory receptors expressed at the NK cell surface. Thus, a balance between receptors that deliver either triggering or inhibitory signals tunes the NK cell-mediated cytotoxicity. The inhibitory NK receptors include the Ig-like Killer Inhibitory Receptors (KIR) which are specific for HLA.A, .B or .C, the HLA-E-specific CD94/NKG2A heterodimer and ILT2, a member of the ILT/LIR family, characterized by a broad specificity for HLA Class I molecules. The molecular nature of the triggering receptors has been revealed, at least in part, by the recent identification or surface molecules that contribute to the process of natural cytotoxicity. These are represented by (1) the family of the Natural Cytotoxicity Receptors (NCR) including NKp46, NKp44, and NKp30. These receptors are selectively expressed by NK cells and recognize still undefined ligands expressed on both normal and transformed target cells; (2) NKG2D and 2B4 molecules, expressed on both NK cells and a subset of cytolytic T cells, that are specific for MICA/B and CD48, respectively. Under physiological conditions, the triggering capability of these receptors is counterbalanced by inhibitory signals generated by the interaction of KIR and/or CD94/NKG2A with the HLA Class I ligands. However, in tumor or virally infected cells, an insufficient expression of Class I molecules may alter this balance. A similar situation occurs when NK cells interact with allogeneic cells (e.g. PHA blasts) expressing HLA Class I alleles for which NK cells do not express specific inhibitory receptors. Under all the above conditions, triggering NK receptors are allowed to transduce activating signals that result in target cell lysis. It is now clear that triggering of NK cells in the process of cytolysis is the result of multiple interactions between different NK receptors or co-receptors and their ligands on target cells, thus underscoring the complexity of the molecular mechanisms leading to NK cell activation.

In this context, the inventors have identified a triggering surface polypeptide expressed on all human NK cells and, at least in some donors, on a small subset of T cells. Said molecule, termed NKp80 in the description and the claims, appears to cooperate with the previously identified triggering receptors to induce an optimal NK cell activation upon interaction with potential target cells.

Analogous polypeptides were prepared which advantageously appeared to be endowed with similar activities.

Said polypeptides, i.e. the isolated, purified, triggering surface molecule NKp80 and analogs, can advantageously be used for raising antibodies.

It is then an object of the invention to provide novel triggering polypeptides able to be involved in NK cell mediated recognition and killing of target cells.

It is another object of the invention to provide antibodies, or fragments thereof, which selectively recognize said polypeptides.

According to still another object, the invention relates to the use of said antibodies for NK cell enrichment and for NK cell natural cytotoxicity regulation.

The polypeptides of the invention are characterized by a triggering NK activity and an amino acid sequence that is at least 80% identical over its entire length to the polypeptide having SEQ ID NO: 1, and the immunogenic fragments thereof.

"Identity", as known in the art, is a relationship between two or more polypeptide sequences, as determined by comparing the sequences. In the art, "identity" also means the degree of sequence relatedness between polypeptide sequences, as determined by the match between strings of such sequences. "Identity" can be readily calculated by known methods, including but not limited to those described in Computational Molecular Biology, Lesk, A. M., ed., Oxford University Press, New York, 1988. Methods to determine identity are designed to give the largest match between the sequences tested. Moreover, methods to determine identity are codified in publicly available computer programs, such as the GAP program in the GCG program package (Devereux, J., et al., Nucleic Acids Research 12(1): 387 (1984), BLAST, BLASTN (Altschul, S. F. et al., J. Molec. Biol. 215: 403-410 (1990), and FASTA (Pearson and Lipman Proc. Natl. Acad. Sci. USA 85; 2444-2448 (1988).

By "immunogenic fragment", it is herein meant any polypeptidic or peptidic fragment which is capable of eliciting an immune response such as (i) the generation of antibodies binding said fragment and/or binding any form of said polypeptides of the invention comprising said fragment, including the membrane receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammal immunoglobulins. Alternatively, an immunogenic fragment also refers to any construction capable of eliciting an immune response as above defined, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

SEQ ID NO: 1 relates to the sequence of the polypeptide expressed when transfecting cells with a vector construct containing cDNA of SEQ ID NO: 2. The transmembrane region is double underlined. Tyrosine residues in the cytoplasmic tail are underlined. Potential N-glycosylation sites are indicated with asterisks.

Figure 3:
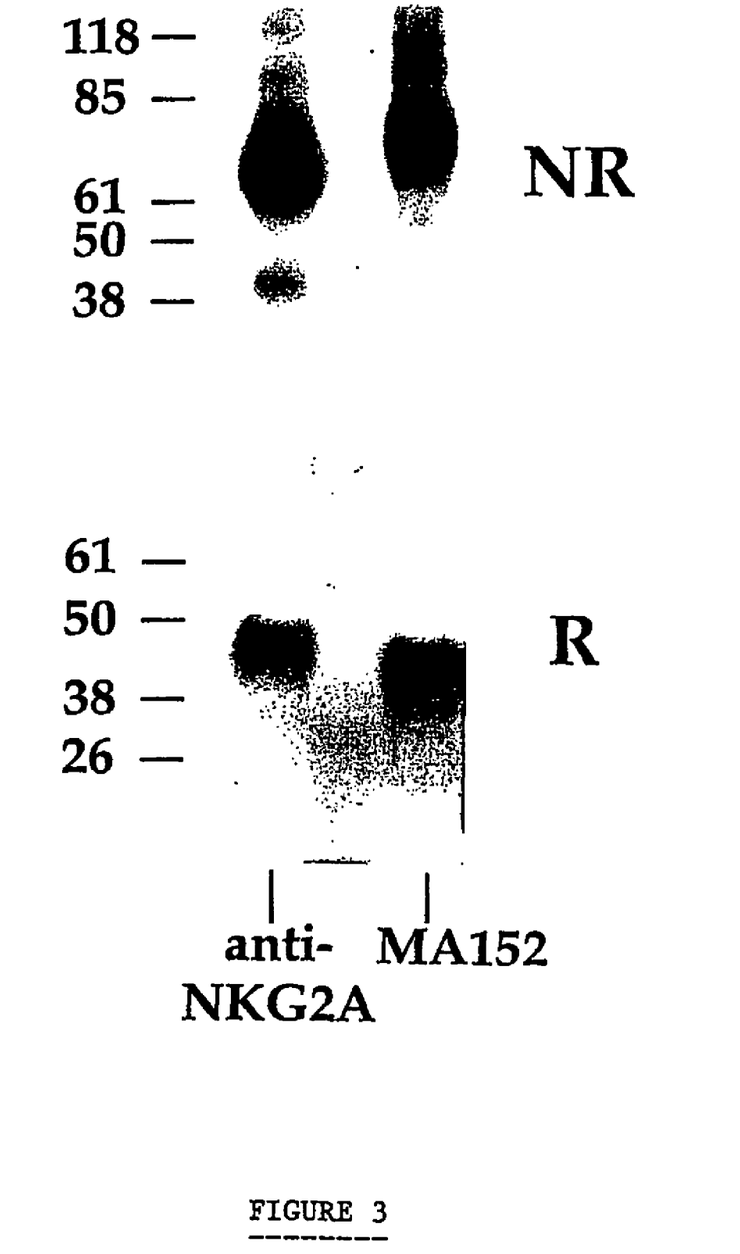

The invention particularly relates to isolated, purified polypeptides, having a molecular weight of 80 kDa in the SDS PAGE profile of FIG. 3 obtained under non-reducing conditions from a lysate from a polyclonal NK cell population, immunoprecipitated with an antibody raised against said polypeptide, and a molecular weight of 40 kDa under reducing conditions.

The invention also relates to polypeptides as expressed by transfecting cells with the cDNA of SEQ ID NO: 2.

A particularly preferred polypeptide, designated by NKp80, corresponds to SEQ ID NO: 1. Such a molecule is selectively expressed by human NK cells and a minor subset of CD3$^+$ T cells.

The present invention also includes analogs of the above defined polypeptides, i.e. polypeptides that vary from the referents by conservative amino acids substitutions, whereby a residue is substituted by another with similar characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. More generally, conservative variants are still capable of acting as a triggering receptor when expressed by NK cells in a receptor appropriate location.

In a further aspect, the invention relates to an antiserum composition which is obtained by immunizing a mammal with at least a polypeptide of the invention and collecting the antiserum thus produced, said polypeptide being optionally coupled to an immunogenicity enhancer.

It also relates to polyclonal antibodies isolated from said antiserum composition, and particularly monoclonal antibodies specifically directed against a polypeptide of the invention.

The invention particularly relates to monoclonal antibodies directed against a polypeptide such as above defined which is reactive with NK cells expressing CD56$^-$ molecules, and a minor subset of CD3$^-$ T cells.

In another aspect, the invention relates to isolated immuno-reactive fragments of any antibody selected from the group comprising the isolated polyclonal antibodies and monoclonal antibodies according to the invention.

Such fragments notably include Fab, F(ab')2, and CDR antibody fragments.

The skilled person will note that humanized antibodies of the invention can be derived therefrom as desired, notably when intended to be administered to a human person. By "immuno-reactive fragments of an antibody", it is herein notably meant any antibody fragment comprising the antigen binding-site. Such fragments thus include F(ab')2 fragments obtained either by enzymatic digestion of said antibody by proteolytic enzymes such as pepsin or papain, and Fab fragments derived thereof by reduction of the sulfhydryl groups located in the hinge regions, as known by any skilled person. Immuno-reactive fragments can also comprise recombinant single chain or dimeric polypeptides whose sequence comprises the CDR regions of the antibody of interest.

The invention more particularly relates to any isolated antibody that is directed against at least a polypeptide of the invention and that does not bind to any B cell surface molecule. Preferred antibodies do not bind monocytes, granulocytes, and preferably do not bind any nucleated cell from peripheral blood except NK cells and a minor subset of CD3$^+$ T cells. Most preferred isolated antibodies do neither bind any NKp45 or NKp44 extracellular portion, nor any other NK cell surface molecule.

Such binding reactions are herein meant as binding reactions such as observed in reactions of the antibody-antigen type under experimental conditions appropriate for such antibody-antigen type recognition reactions.

Such binding reactions can be achieved e.g. by contacting a leucocyte suspension from peripheral blood with the antibody, detecting the immune complexes thus formed e.g. by contacting with a secondary anti-immunoglobulin reagent carrying a fluorescent label, and enumerating and identifying cells binding the antibody using a flow cytometer such as Beckman-Coulter XL. Alternatively, antibodies can be directly labelled with fluorochromes for flow cytometry detection. Alternatively, after being contacted with the antibody of interest as described above, the same leucocyte suspension can be contacted with a fluorochrome-conjugated antibody binding specifically to a leucocyte subset such as CD3 antibody UCHT-1 which binds specifically to T-cells, thus allowing a phenotypic definition of the leucocyte subset binding the antibody of interest. Several experiments of dual labelling as described can be performed, using a panel of subset-specific antibodies, to further delineate the cellular reactivity of the antibody of interest.

Preferred antibodies of the invention can induce (i) a statistically significant increase in a NK cell-mediated cytotoxicity in a redirected killing assay, (iii) an increase in cytoplasmic Ca concentration upon antibody crosslinking on the surface of NK cells, by crosslinking reagents such as polyclonal anti-immunoglobulin reagent or anti-immunoglobulin reagent coated beads, (iii) an inhibition of NK cell cytotoxicity on NKp80 sensitive targets, such as PHA blasts.

Any isolated antibody of the invention can be coupled to any appropriate label for visualisation purposes. Such labels include e.g. the fluorescent labels, the radioactive labels, the enzymatic labels.

In another aspect, the present invention relates to any solid support on which is attached at least an isolated antibody that is directed against at least a polypeptide of the invention. Any solid support allowing said attachment is appropriate. Particularly appropriate solid supports include paramagnetic microspheres that can be used as affinity matrix such as Dynabeads® from Dynal a.s. (Oslo, Norway), sub-microscopic MACS microbeads from Miltenyi Biotec GmbH (Gladbach, Germany), semi-permeable substrate consisting of an array of hollow fibers as described in U.S. Pat. No. 5,763,194, dense particles allowing separation by sedimentation as described in U.S. Pat. No. 5,576,185.

An advantageous embodiment of these solid supports of the invention comprises the presence, on said supports, of anti-NKp46 and/or anti-NKp44 antibodies, or immunogenic fragments or derivatives thereof further attached on said solid support. As illustrated below, the polypeptide receptor of the invention can indeed cooperate in additional or synergetic ways with other receptors such as the NKp46 and/or NKp44 receptors.

In still another aspect, the invention relates to the antibodies such as above defined or fragments thereof coupled to a marker.

The present invention also relates to any hybridoma that produces a monoclonal antibody that is directed against a polypeptide of the invention. Monoclonal antibodies of the invention can be prepared using any technique that provides for the production of antibody molecules by recovering spleen cells after the immunisation step and establishing continuous cell lines in culture. These include, but are not limited to, the original techniques of Kohler and Milstein, Nature, 265:495-497 (1975), modified as described in Anderson et al., J. Immunol., 143:1899 (1989), the content of which is hereby incorporated by reference.

Screening procedures that can be used to screen hybridoma cells producing antibodies to said polypeptides include, but are not limited to, (1) enzyme-linked immunoadsorbent assays (ELISA), (2) immunoprecipitation and (3) fluorescent activated cell sorting (FACS) analyses, (4) functional assays. Many different functional assays can be used to screen for anti-polypeptides monoclonal antibodies, such as redirected killing assays.

Initial screening is preferably conducted by screening hybridoma supernatants by flow cytometry for their reactivity with NK cells, but not with B cells, and monocytes. Further characterization of the hybridomas can be conducted by testing on purified populations of lymphoid and non-lymphoid cells by indirect immunofluorescence assays and flow cytometry, substantially as described in the Examples herein. Monoclonal antibodies that recognize a polypeptide epitope particularly a NKp80 epitope, will react with an epitope that is present on practically the whole NK cell population and a small subset population of CD3$^-$ T cells, but will not significally react with most CD3$^+$ T cells or CD20$^+$ B cells. In preferred embodiments, the antibody will also be unreactive with monocytes, granulocytes, platelets, and red blood cells.

Monoclonal antibodies that compete with such antibodies in competition assays well known to persons skilled in the art are likely to recognize essentially the same epitopes.

Once the desired hybridoma has been selected and cloned, the resultant antibody may be produced in one of two major ways. The purest monoclonal antibody is produced by in vitro culturing of the desired hybridoma in a suitable medium for a suitable length of time, followed by the recovery of the desired antibody from the supernatant. The length of time and medium are known or can readily be determined. This in vitro technique produces essentially monospecific monoclonal antibody, essentially free from other species of anti-human immunoglobulin. However, the in vitro method may not produce a sufficient quantity or concentration of antibody for some purposes, since the quantity of antibody generated is only about 50 µg/ml.

To produce a much larger quantity of monoclonal antibody, the desired hybridoma may be injected into an animal, such as a mouse.

Preferably the mice are syngeneic or semi-syngeneic to the strain from which the monoclonal antibody-producing hybridomas were obtained. Injection of the hybridoma causes formation of antibody producing tumors after a suitable incubation time, which will result in a high concentration of the desired antibody (about 5-20 mg/ml) in the ascites of the host animal.

Antibody molecules can be purified by known techniques e.g. by immunoabsorption or immunoaffinity chromatography, chromatographic methods such as high performance liquid chromatography or a combination thereof.

Following these protocols, any person skilled in this area of technology can readily isolate hybridomas that produce monoclonal antibodies exhibiting specificity for said polypeptides, particularly for NKp80. It is thus contemplated that the present invention encompasses all monoclonal antibodies exhibiting the desired anti-polypeptide characteristics.

In a further aspect, the invention relates to any composition of the anti-antiserum type which is such as obtained by immunizing a mammalian with at least one substance chosen among the group consisting of the compositions of the antiserum-type according to the invention, the isolated antibody-antigen type compounds of the invention, the antibodies and monoclonal antibodies of the invention, this at least one substance being optionally coupled to an immunogenicity enhancer, and collecting the anti-antiserum thus produced and to pharmaceutical compositions comprising the same.

As illustrated by the Examples, the polypeptides of the invention are useful as NK cell markers.

With respect to NKp80, more particularly, said molecule is almost exclusively expressed by NK cells, both freshly isolated and cultured in the presence of one, two or multiple cytokines such as IL-2, IL-12, IL-15, FLT-3 ligand, SCF, thus representing an optimal marker for NK cell identification.

The present invention thus relates to a method for detecting NK cells in a sample, comprising using a compound selected in the group comprising an antiserum such as above defined, an antibody or immuno-reactive fragment thereof such as above defined, or a nucleic acid having SEQ ID NO: 2 or a part thereof.

According to a preferred embodiment, said method comprises:

contacting said sample with a compound selected in the group comprising said antiserum composition, antibodies and immuno-reactive fragments thereof, such as above defined, optionally attached to a marker or to a solid support, under conditions appropriate for immune complex formation, and with an anti-CD3 antibody with a distinct marker, then detecting CD3$^-$, polypeptide positive cells, particularly NKp80$^+$ cells.

According to another embodiment, said method comprises:

contacting said sample with a compound selected from a polynucleotide or an oligonucleotide of the gene coding for a polypeptide as above defined, under conditions appropriate for the formation of hybridation products, and detecting, and quantifying if desired, the hybridation products when formed.

The invention also relates to a method for the removal of NK cells from a sample, comprising:

contacting said sample with a compound selected from the group comprising an antiserum composition, antibodies or immuno-reactive fragments thereof, such as above defined, and eliminating the immune complexes when formed.

A method for enrichment of NK cells from a sample is also part of the invention. Such a method comprises:

contacting said sample with a compound selected from the group comprising an antiserum composition, antibodies or immuno-reactive fragments, such as above defined, and recovering the immune complexes when formed.

According to another aspect, the invention relates to kits for detecting NK cells in a sample or for the enrichment of NK cells from a sample.

Such kits comprise a compound selected from the group comprising an antiserum composition or antibodies, such as above defined, conjugated to markers or immuno-reactive fragments such as above defined, coupled to a solid support such as magnetic beads.

The invention also relates to kits for detecting NK cells, comprising an anti-polypeptides such as above defined coupled to a first marker and an anti-CD3 antibody coupled a second marker.

According to still another aspect, the invention relates to a method for stimulating NK cell cytotoxicity, comprising:
contacting said NK cells under physiological conditions with a compound selected from the group comprising an antiserum composition and antibodies, such as above defined, and
crosslinking the immune complexes on the cell surface when formed with a compound selected from the group comprising an anti-antibody or anti-antibody coated beads.

A method for inhibiting NK cells cytotoxicity is also encompassed by the invention. Such a method comprises contacting NK cells under physiological conditions with an immuno-reactive fragment such as above defined in order to block NKp80 interaction with its ligand.

The invention also relates to pharmaceutical compositions for NK cell depletion, comprising an effective amount of a compound selected from the group comprising an antiserum composition or antibodies, such as above-defined, together with a pharmaceutically acceptable vehicle.

It also relates to pharmaceutical compositions for inhibiting NK cell cytotoxicity, comprising an effective amount of an immuno-reactive fragment, such as above-defined, together with a pharmaceutically acceptable vehicle.

According to another object, transfectants expressing the above defined polypeptides are also part of the invention. Said transfectants advantageously comprise a cDNA having SEQ ID NO: 2.

The transfectants of the invention are particularly useful for screening either triggering NK cells or a sub-population of T cell molecules, or inhibitors of said NK and T cells.

The invention thus also relates to a method for screening molecules having a triggering or an inhibitory NK cell or T cell sub-population activity, comprising using a transfectant such as above defined, and selecting the tested molecules which significantly modify the NKp80-mediated signals in the transfectant compared to the non transfected control.

According to still another object, the invention relates to the use of the above defined polypeptides as markers for typing LDGL and for identifying abnormal cells in the whole lymphocyte population of a patient.

The analysis of the expression of NKp80 in patients affected by LGL expansion has indeed revealed that all CD3⁻ LGL expansions expressed NKp80 and that among the CD3⁺ LGL expansions analyzed, a major part expressed NKp80, while CD16 and CD56 were also observed. Such data demonstrate the interest of NKp80, and analogs, as markers as above defined.

These and other features and advantages of the invention will be further apparent from the following examples. These examples are given for illustrative purposes only, and are in no way intended to restrict the scope of the present invention. Alternatives embodiments intended by any skilled person are encompassed by the present invention.

In these examples, reference is made to FIGS. 1 to 7 which illustrate, respectively.

Panel a: purified NK cells were stained with mAbs specific for the indicated molecules and analyzed by immunofluorescence and FACS analysis. PE-conjugated isotype-specific goat anti-mouse was used as second reagent.

Panel b: PBMC from two representative donors were depleted of adherent cells and analyzed by double fluorescence for the expression of MA152-reactive molecules in combination with the indicated surface markers. Cells were stained with mAbs to the indicated molecules followed by FITC- or PE-conjugated isotype-specific goat anti-mouse second reagents. The contour plots were divided into quadrants representing unstained cells (lower left), cells with red fluorescence only (upper left), cells with red and green fluorescence (upper right) and cells with green fluorescence only (lower right).

Representative polyclonal NK cell populations (panels A and B), TCRαβ⁺ cell populations (panels C and D) and TCRγζ⁻ cell populations (panels E and F) were comparatively analyzed by the use of MA152 and anti-CD56 mAbs. PE-conjugated isotype-specific goat anti-mouse was used as second reagent.

FIG. 3: the biochemical characterization of MA152 mAb-reactive molecule. Lysates derived from a $^{125}$I labeled polyclonal NK cell population were immunoprecipitated with Z199 (anti-NKG2A) and MA152 mAbs. Samples were analyzed in an 8% or 11% SDS-PAGE under non-reducing (NR) or reducing (R) conditions, respectively. Molecular weight markers (kD) are indicated.

Panel a: Fresh purified NK cells were analyzed in a redirected killing assay against the FcγR⁺ P815 target cell line (E/T ratio 10:1) either in the absence or in the presence of mAbs to the indicated surface molecules.

Panel b: A polyclonal activated NK cell population was analyzed in redirected killing against P815 cells (E/T ratio 2:1) either in the absence or in the presence of graded amounts of anti-NKp80 (MA152, IgG1) (filled circles), anti-NKp46 (BAB281, IgG1) (open squares) or anti-CD56 (c218, IgG1) (triangles) mAbs.

Panel c: The same representative polyclonal NK cell population was analyzed for Ca⁺⁺ mobilization after pre-treatment with anti-NKp80 (MA152) mAb (IgG1) or anti-CD56 (c218) mAb (IgG1). At the time indicated, Goat Anti-Mouse (GAM) was added to obtain optimal cross-linking of the NKp80 or the CD56 molecules at the cell surface.

6 representative UK cell clones were comparatively analyzed for the expression of NKp80 and NKp46 molecules (left) and assessed for cytolytic activity against P815 target cells (right) either in the absence of mAb (■) or in the presence of anti-NKp80 (▦), anti-NKp46 (□) or anti-CD 16 (▩) mAbs.

Three representative NK cell clones were analyzed for cytolytic activity against allogeneic PHA-induced T cell blasts either in the absence of mAb or in the presence of mAbs against the indicated surface molecules.

Panel a: 293T cells, transfected with VR1012-ML, were stained with MA152 or LAP171 mAbs followed by PE-conjugated isotype-specific goat anti-mouse and analyzed by flow cytometry. White profiles represented cells incubated with the second reagent alone (negative control).

Panel b: The predicted transmembrane region is double underlined. Tyrosine residues in the cytoplasmic tail are underlined. Potential N-glycosilation sites are indicated with asterisks.

MATERIALS AND METHODS

Monoclonal Antibodies (mAbs)

MA152 (IgG1) and LAP171 (IgG1) mAbs were conventionally derived by immunizing two 5-wk-old Balb/C mice with the NK clones KK4 and LAN 59, respectively. Both NK cell clones displayed the following surface phenotype: $CD3^-$, $CD56^+$, $CD16^-$, $NKp46^+$, $NKp30^-$, $NKp44^-$, $NKG2D^+$, $2B4^-$, NKG2A. After cell fusions, the mAbs were selected on the basis of their ability to selectively stain fresh and/or activated NK cell populations.

The following mAbs were used: JT3A (IgG2a, anti-CD3), BAB281 (1) (IgG1, anti-NKp46), Z231 (2) (IgG1, anti-NKp44), AZ20 (3) (IgG1, anti-NKp30), c127 (IgG1, anti-CD16), c218 (IgG1, anti-CD56) (5), A6-136 (IgM, anti-HLA class I), PP35 (38) (IgG1, anti-h2B4).

Purification of Peripheral Blood Lymphocytes (PBL) and Generation of Polyclonal or Clonal NK and T Cell Populations Peripheral blood lymphocytes (PBL) were derived from healthy donors by Ficoll-Hipaque.RTM. gradients and depletion of plastic-adherent cells. In order to obtain enriched NK cells, PBL were incubated with anti-CD3 (JT3A), anti-CD4 (HP2.6) and anti-HLA-DR (D1.12) mAbs (30 min at 4° C.) followed by goat anti-mouse coated Dynabeads® (Dynal, Oslo, Norway) (30 min at 4° C.) and immunomagnetic depletion (1, 2).

$CD3^-$ $4^-$ $DR^-$ cells were used in cytolytic assays or cultured on irradiated feeder cells in the presence of 100 U/ml rIL-2 (Proleukin, Chiron Corp., Emeryville, USA) and 1.5 ng/ml PHA (Gibco Ltd, Paisley, Scotland) in order to obtain polyclonal NK cell populations or, after limiting dilution, NK cell clones.

In order to obtain polyclonal $TCR\gamma\delta^+$ T cell population, PBL were depleted for $CD4^-$ and $CD8^+$ cells and cultured on irradiated feeder cells in the presence of 100 U/ml rIL-2 and 1.5 ng/ml PHA (5).

Flow Cytofluorimetric Analysis

Cells were stained with the appropriate mAb followed by PE- or FITC-conjugated isotype-specific goat anti-mouse second reagent (Southern Biotechnology Associated, Birmingham, Ala.). Samples were analyzed by one- or two-color cytofluorimetric analysis (FACScan Becton Dickinson & Co, Mountain view, Calif.) as previously described (1,2).

Cell Lines and Cytolytic Assays

The $Fc\gamma R^+$ P815 (murine mastocytoma) target cell line was used for redirected killing experiments (1). PHA blasts were obtained by culturing for three days PBL with 1.5 ng/ml PHA (Gibco). After this period of time, cells were washed and cultured in medium supplemented with 10% FCS and 100 U/ml of rIL2.

Cells were tested for cytolytic activity in a 4-h $^{51}Cr$-release assay either in the absence or in the presence of various mAbs. The concentrations of the various mAbs were 10 µg/ml for the masking experiments and 0.5 µg/ml for the redirected killing experiments. The E/T ratios are indicated in the text.

Determination of Intracellular Free Calcium $[Ca^{++}]i$ Increase

Determination of $[Ca^{++}]i$ was performed as previously described (6). Fura-2-labeled NK cells were incubated for 30 min at 4° C. with saturating amounts of anti-NKp80 mAb (MA152) or isotype matched anti-CD56 mAb (c218). Cross-linking of the receptor was obtained by adding into the cuvette 20 µg/ml of affinity purified Goat Anti-Mouse antiserum (GAM) (ICN Biomedicals, Aurora, Ohio).

LDGL Patients

Fifteen patients (8 men and 7 women, mean age 56±12) were studied. The diagnosis was made according to the recently reported criteria (7). In all cases, a chronic lymphocytosis (lasting more than 6 months) sustained by at least 2,000 GL/mm was demonstrated in peripheral blood. At the time of the study, all patients had never received any therapy, with exception of patient #10 that was under immunosuppressive therapy for pure aplasia. Patients # 6, 8, 9, 10, 12, 15 expressed the $CD3^+$ $CD4^-$ $CD8^+$ $TCR\alpha\beta^+$ phenotype; patients # 7, 13 and 14 showed the $CD3^+$ $CD4^-$ $CD8^+$ $TCR\alpha\beta^+$ phenotype and patient # 11 showed the $CD3^+$ $CD4^-$ $CD8^-$ $TCR\gamma\delta^+$ phenotype.

Molecular analysis by Southern blot showed the presence of a monoclonal rearrangement of TCR $\beta$ and/or $\gamma$ genes. Two out of five patients with a $CD3^-$ NK type LDGL (# 3 and 5, both women) were analyzed for clonality by evaluating the RLF polymorphism and the methylation pattern of the X-linked PGK gene and both cases were shown to be characterized by a polyclonal proliferation of GL.

Biochemical Characterization of NKp80 Molecules $30 \times 10^6$ cells were labeled with $^{125}I$ (NEN, Boston, Mass.), lysed in 1% NP-40 and immunoprecipitated with Sepharose-PA (Pharmacia Biotech Inc. Piscataway, N.J.)-coupled Z199 (anti-NKG2A) and MA152 (anti-NKp80) mAbs. Samples were analyzed by discontinuous SDS-PAGE under non-reducing or reducing conditions (5% 2-mercaptoethanol) (2).

Library Screening by cDNA Expression in COS-7 and SIB-Selection

The library screening was performed as previously described (8). Briefly, the cDNA library, fractionated in ten different pools, was transiently transfected in COS-7 cells using non-liposomal FuGene-6 reagent (Roche, Monza, Italy) following the manufacture's instruction. Selection of positive pools was performed by immunocytochemical staining using the specific anti-NKp80 mAb LAP 171 and sib selection.

DNA Sequencing and Protein Analysis

DNA sequencing was performed using d-Rhodamine Terminator Cycle Sequencing kit and a 377 ABI automatic sequencer (Perkin Elmer-Applied Biosystems). The analysis of the putative protein coded by the ML cDNA was performed using the GeneWorks 2.5.1N and the site World Wide Web//genome.cbs.dtu.dk/htbin/hph-webface.

Transient Tranfection 293T cells ($4 \times 10^5$/plate) were transfected with VR1012/ML using FuGene-6 reagent. After 48 h, transfected cells were stained with LAP171 and MA152 anti-NKp80 mAbs, followed by isotype-specific PE-conjugated goat anti-mouse second reagent and analyzed by flow cytometry using a FACSort (Becton Dickinson).

Results

Identification of a Novel NK Cell Surface Molecule

Figure 1:
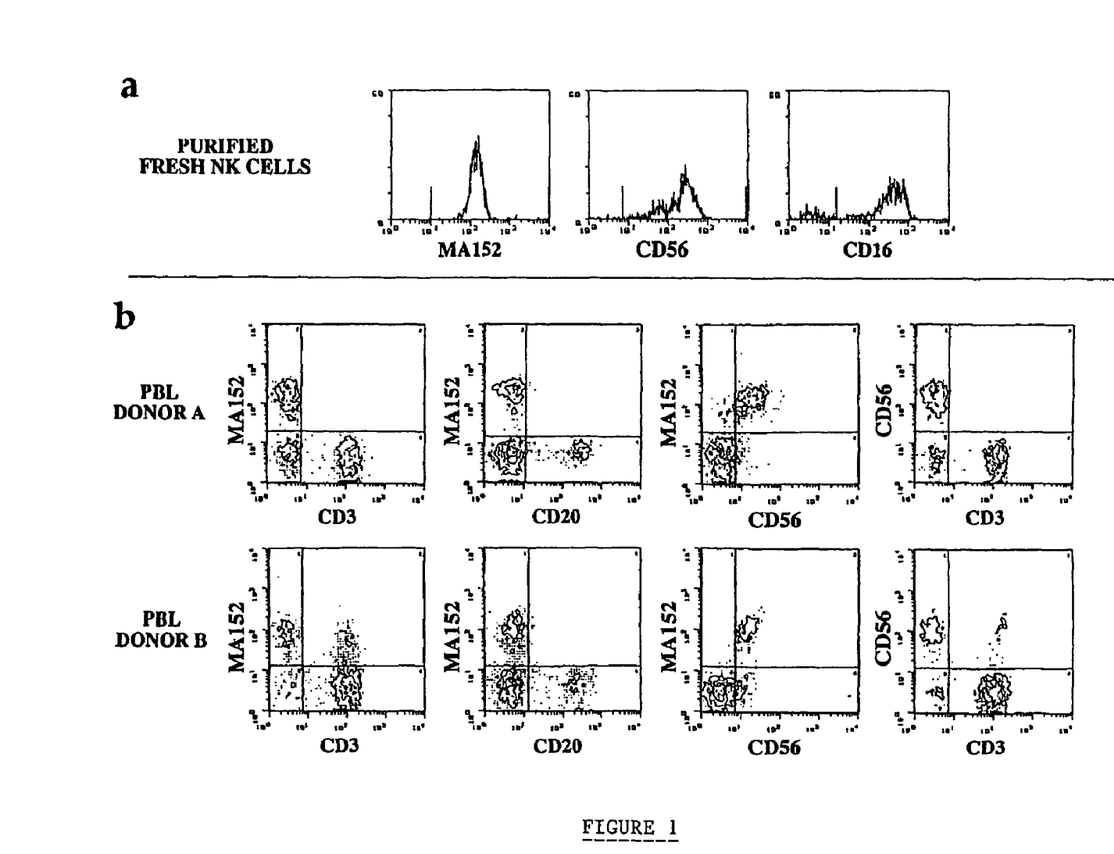
FIG. 1: the cytofluorimetric analysis of MA152-reactive molecules on peripheral blood lymphocytes (PBL), MA152 being a monoclonal antibody of the invention.

Mice were immunized with the KK4 human NK cell clone. After cell fusion, a mAb termed MA152 was selected on the basis of its specific reactivity with fresh and/or cultured polyclonal NK cell populations. As shown in FIG. 1a, MA152 mAb stained all freshly isolated purified CD56+ HLA DR− CD3− NK cells including a minor $CD16^-$ $CD56^+$ cell subset. Moreover, analysis of unfractionated peripheral blood lymphocytes (PBL) showed that, in most donors, the reactivity of MA152 mAb was restricted to CD3$^-$ CD56$^+$ cells while CD3$^+$ T cells were not stained. However, in some donors characterized by a minor subset of CD3$^+$ CD56$^+$ T cells, the proportion of CD3$^+$ MA152$^+$ cells paralleled that of CD3$^+$ CD56$^+$ cells (FIG. 1b), thus showing that MA152 mAb-reactive molecules are also expressed by this T cell subset. This concept was confirmed by double fluorescence analysis showing that most MA152$^+$ cells co-expressed CD56. MA152 mAb did not stain peripheral blood CD20$^-$ B cells (FIG. 1b), granulocytes or monocytes nor reacted with T cell lines (Jurkat, H9, MOLT4), B cell lines (C1R, LCL 721.221, RAJI), myeloid cell lines (U937) and the erythroblastoids cell line K562 (not shown). Interestingly, none of the NK cell lines analyzed including NKL, NK3.3 and YT, was stained by MA152 mAb (not shown).

The cell surface distribution of MA152 mAb-reactive molecules was analysed in activated (IL-2 cultured) NK cells derived from 15 different donors. Virtually all the polyclonal NK cell populations or NK cell clones analyzed were stained by MA152 mAb (FIG. 2), although the mean fluorescence intensity was generally lower than in resting NK cells.

Figure 2:
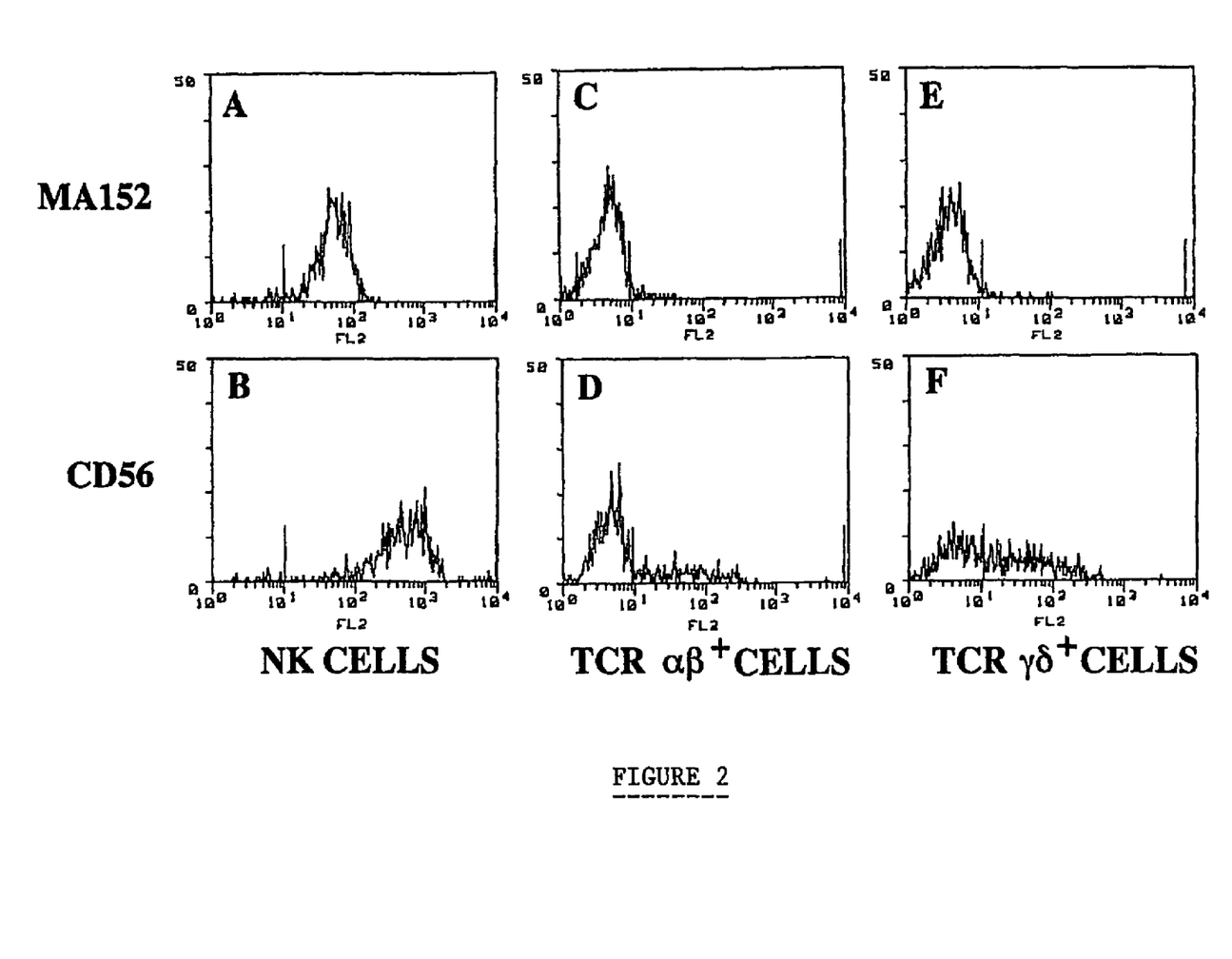
FIG. 2: the expression of MA152-reactive molecule on activated lymphocyte populations.

PHA-activated clonal or polyclonal T cell populations (either αβ or γδ) did not react with MA152 mAb (FIG. 2). It is of note that a fraction of these T cells expressed CD56, thus providing evidence that the surface molecules recognized by MA152 mAb and CD56 are not necessarily co-expressed at the cell surface.

Cell lysates obtained from IL-2 cultured polyclonal NK cells that had been surface labeled with $^{125}$I, were immunoprecipitated with MA152 mAb and analyzed by SDS-PAGE (FIG. 3). Under non-reducing conditions a band of approximately 80 kD could be detected that, after reduction, displayed a molecular mass of ≈40 kD. These data indicate that the surface molecule (hereafter termed NKp80) recognized by MA152 mAb is expressed at the NK cell surface as a dimer.

Similar results were obtained with a second anti-NKp80 mAb (LAP171 IgG1) isolated from a different fusion.

Figure 4A:
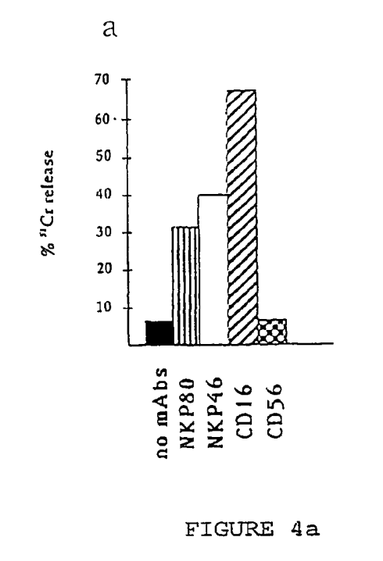
FIG. 4: the triggering of NK cell-mediated cytolytic activity and Ca⁺⁺ mobilization by anti-NKp80 mAb.
Figure 4B:
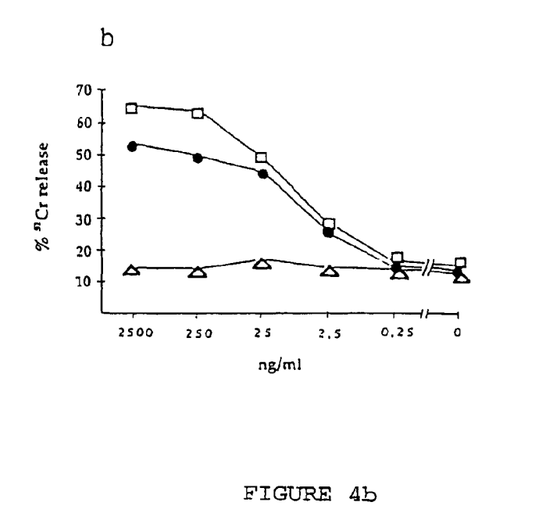
Figure 4C:
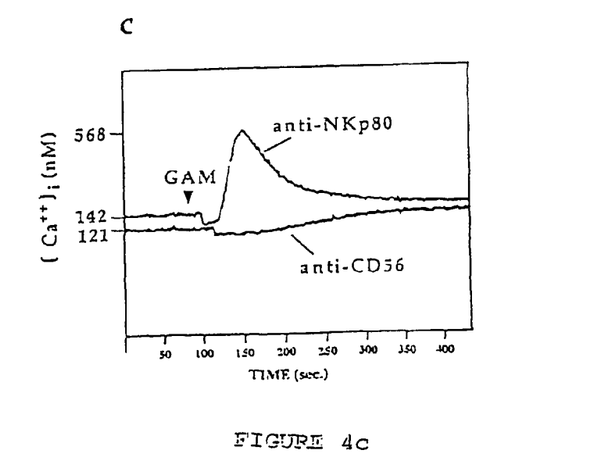

Cross-linking of NKp80 Induces Ca$^{++}$ Mobilization and Triggering of Cytotoxicity in Both Resting and Activated NK Cells Further experiments were performed to analyse any effect resulting from the cross-linking of NKp80 on the cytolytic activity of human NK cells. To this end, freshly isolated ("resting") or IL-2 cultured ("activated") NK cells were analyzed in a redirected killing assay against the FcγR$^+$ murine P815 target cell line, either in the absence or in the presence of MA152 mAb. The NK cell responses to MA152 mAb were compared to those induced by anti-CD16 or anti-NKp46 mAbs. An isotype matched anti-CD56 mAb was used as a control. As shown in FIG. 4, similarly to anti-CD16 or anti-NKp46 mAbs, MA152 mAb induced target cell lysis by both resting (panel a) and activated (panel b) NK cells.

It was then evaluated whether NK cell triggering via NKp80 could induce Ca$^{++}$ mobilization. As shown in FIG. 4 panel c, a sharp (Ca$^{++}$)i increase was detected in polyclonal NK cell populations after mAb-mediated cross-linking of NKp80. Note that (Ca$^{++}$)i increments occurred only in the presence of a goat anti-mouse second reagent, allowing efficient cross-linking of NKp80 surface molecules.

Figure 5:
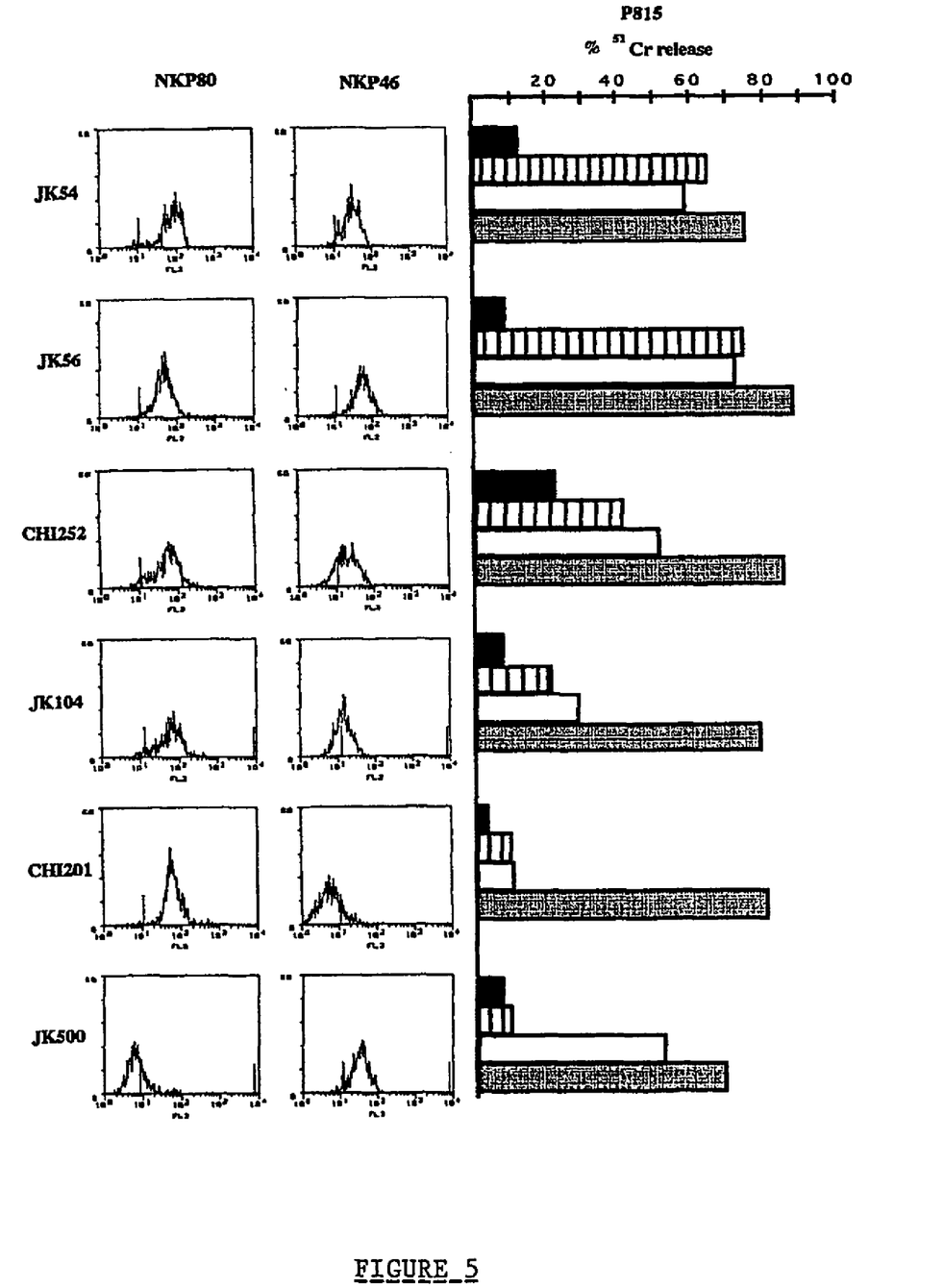
FIG. 5: the clonal heterogeneity of the triggering responses to anti-NKp80 mAb.

The cytolytic responses to anti-NKp80 mAb in redirected killing assays against P815 target cells were further evaluated in a large panel of NK cell clones (>100) derived from different donors (FIG. 5). In most clones anti-NKp80 mAb induced cytolytic responses. However, even among clones displaying similar surface densities of NKp80 (FIG. 5), substantial differences existed in the magnitude of cytolytic responses to anti-NKp80 mAb. In general, strong cytolytic responses to anti-NKp80 mAb correlated with high surface densities of NKp46 molecules (NKp46$^{bright}$ clones) (see the representative JK54 and JK56 NK cell clones). On the contrary, NK cells characterized by a NKp46$^{dull}$ phenotype (see clones CHI201 and JK104), although expressing high levels of NKp80 were poorly cytolytic in response to anti-NKp80 mAb. In agreement with previous results, these NKp46$^{dull}$ clones displayed poor responses to anti-NKp46 mAb, although had a normal cytolytic potential as assessed by their ability to respond to anti-CD16 mAb.

As mentioned above, all NK cell clones expressed NKp80, however, infrequent clones expressed low levels of NKp80. These NKp80$^{dull}$ clones (see the representative clone JK500) were unresponsive to anti-NKp80 mAb in redirected killing assays (FIG. 5). Remarkably, some of these clones were characterized by a NKp46$^{bright}$ phenotype and displayed strong cytolytic responses to anti-NKp46, anti-CD16 (FIG. 5), anti-NKp44 or anti-NKp30 (not shown) mAbs. Thus, the surface density (bright vs. dull) of NKp80 does not appear to correlate either with the expression of NCR or with the expression of other triggering surface molecules (including CD16, CD2, CD69, CD70 and 2B4). In addition, no correlation was found with the expression of HLA-class I specific inhibitory receptors (including KIR, ILT-2/LIR-1 or CD94/NKG2A) (not shown).

Figure 6:
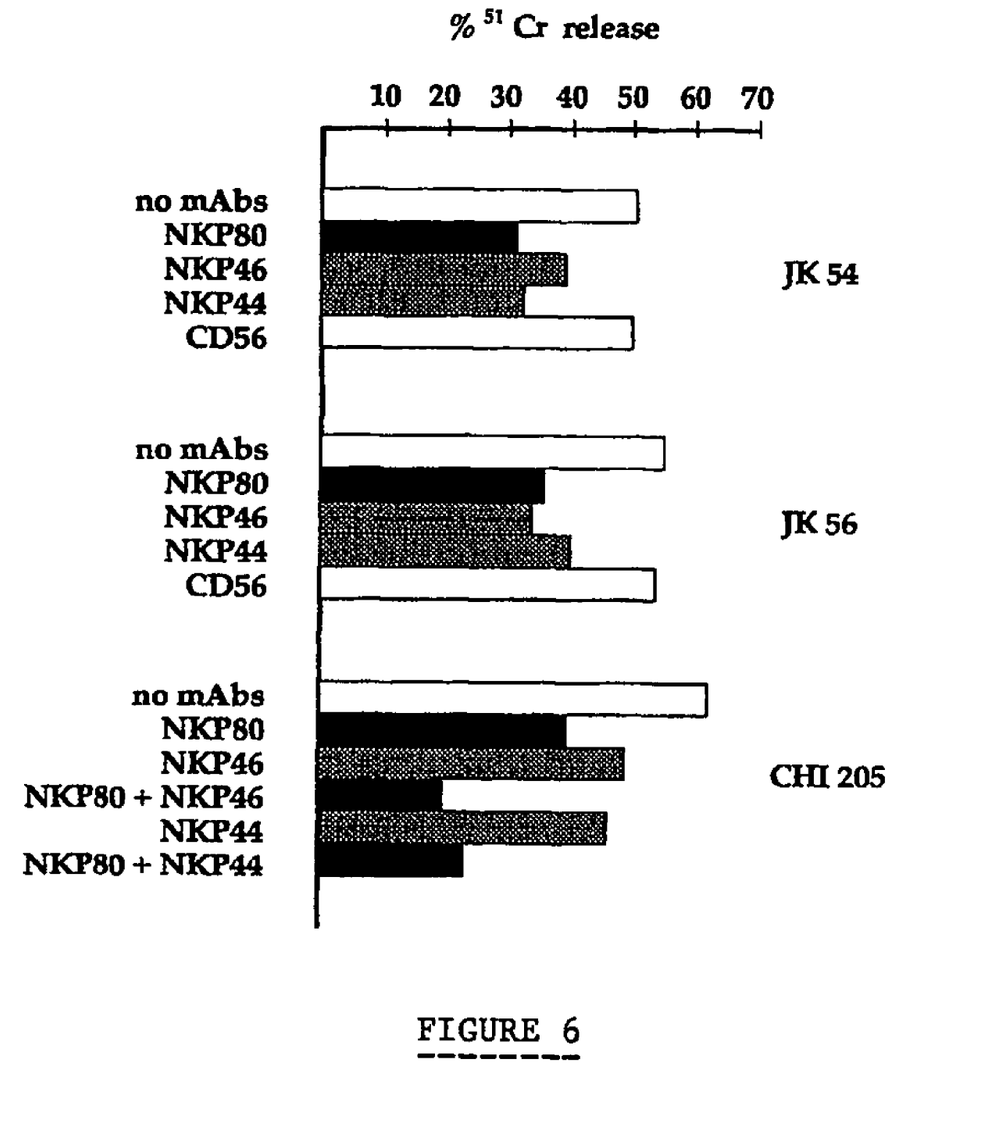
FIG. 6: the MAb-mediated masking of NKp80 inhibits the NK cell-mediated cytotoxicity against PHA-induced T cell blasts.

MAB-mediated Masking of NKp80 Inhibits the NK-mediated Cytotoxicity Against PHA-induced T Cell Blasts NK cells are capable of killing not only tumor but also normal target cells provided that the inhibitory NK receptors are not engaged by their HLA Class I ligands expressed on target cells. As previously shown, the triggering receptors involved in killing of both tumor and normal target cells are primarily represented by the various NCR. Since both the cellular distribution and the triggering function of NKp80 are reminiscent of those of NCR, experiments were carried out to study the NKp80 role in the NK-mediated lysis of tumor cells or (allogeneic) PHA-induced T cell blasts as a source of normal cells. The analysis of a panel of tumor target cells including melanomas, lung and liver carcinomas, EBV-transformed B cell lines as well as leukemic T cell lines including Jurkat and HSB-2 did not show any substantial involvement of NKp80 in target cell lysis by polyclonal UK cell populations or NK cell clones (as revealed by MA152 mAb-mediated masking). On the contrary, lysis of suitable allogeneic PHA blasts was inhibited by mAb-mediated masking of NKp80. The inhibitory effect of masking NKp80 was comparable to that obtained by masking NKp46, NKp44 (FIG. 6) or NKp30 (not shown). Moreover, the combined use of anti-NKp80 and anti-NCR mAbs resulted in an incremented inhibitory effect. Accordingly, NKp80 appears to function as an activating receptor recognizing a ligand expressed by normal (PHA-induced) T cell blasts. Surprisingly, lysis of the leukemic cell lines Jurkat and HSB-2, i.e. the leukemic counterparts of T lymphoblasts, was NKp80-independent.

NKp80 Expression in Lymphoproliferative Diseases of Granular Lymphocytes (LDGL)

LDGL are characterized by a chronic proliferation of either CD3$^+$ or CD3$^-$ circulating Large Granular Lymphocytes (LGL). Determination of clonality or oligoclonality as well as analysis of CD16 (often expressed in CD3$^+$ LGL expansions), the expression of TCRVαβ and CD8/CD4 are usually applied to characterize CD3+ LDGL (27, 28, 29). In addition, expression of HLA class I-specific inhibitory receptors has been detected in a fraction of CD3 or CD3+ LGL expansions. Table I summarizes the distribution of NKp80 and other NK-related surface antigens expressed by peripheral lymphocytes derived from 15 LDGL patients.

TABLE 1

Expression of NKp80 in LDGL patients

| Cases # | CD3 | NKp80 | CD56 | CD16 |
| --- | --- | --- | --- | --- |
| 1, 2, 3, 4 | − | + | + | + |
| 5 | − | + | − | + |
| 6, 7 | + | + | + | + |
| 8 | + | + | + | − |
| 9, 10, 11 | + | + | − | + |
| 12, 13 | + | − | − | + |
| 14, 15 | + | − | + | − |

Five were represented by CD3− whereas the remaining were CD3+ LGL expansions. All the CD3− LGL expressed NKp80 and CD16 while only 4 out of 5 expressed CD56. Remarkably, both NKp46 and NKp30 NCR were expressed at low levels in all CD3− LGL expansions analyzed. Accordingly, in redirected killing assays anti-NKp46 or anti-NKp30 mAbs induced poor cytolytic responses comparable to those of typical NCR$^{dull}$ NK clones derived from normal individuals. Moreover, in line with the above results, poor cytolytic responses to anti-NKp80 mAbs could be observed. In contrast, anti-CD16 mAb induced strong cytolytic responses in all CD3-LGL expansions analyzed (not shown).

None of the CD3+ LGL (one TCRγδ+ and nine TCRαβ+) expressed NKp46 or NKp30. On the other hand, although NKp80 is infrequently expressed by normal T cells, it was expressed on 6/10 CD3+ LGL. The combined use of anti-NKp80, anti-CD16 and anti-CD56 mAbs led to the identification of different surface phenotypes in CD3+ LGL. Thus, 2/10 were NKp80+ CD56+ CD16+, 1/10 was NKp80+ $^{CD}$56+ CD16−, 3/10 were NKp80+ CD56− CD16+, 2/10 were NKp80− CD56− CD16+ and 2/10 were NKp80− CD56+ CD16−.

The combined analysis of the surface expression of NKp80 and other markers (such as CD16 and CD56) will then enable to precisely identify CD3+ LGL cells within the whole lymphoid population of the patients.

Molecular Cloning of the cDNA Encoding the NKp80 Molecule

Figure 7:
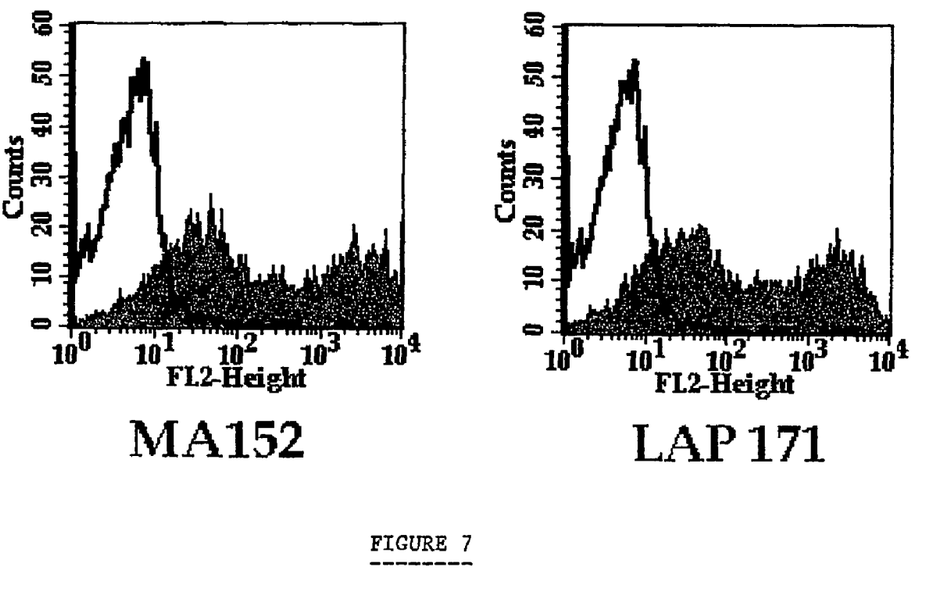
FIG. 7: the NKp80 surface expression in 293T cells transfected with V1012-ML construct and predicted amino acid sequence.

The cDNA coding for the NKp80 molecule was identified by using an expression cloning strategy. This cDNA, termed ML, transiently transfected in 293T cells allowed the surface expression of a molecule that was brightly stained by both anti NKp80 mAbs (FIG. 7, panel a).

Nucleotide sequence analysis revealed that ML cDNA contained a 696 bpORF encoding a 231 amino acid type II transmembrane protein belonging to the C-type lectin-like family with a predicted polypeptide backbone of about 26.5 kD. (FIG. 7, panel b). This molecule displayed a 39 aminoacids (aa) cytoplasmic tail characterized by two tyrosine-based motifs that do not belong to typical ITIM or ITAM sequences. A transmembrane region (23 aa), characterized by the absence of charged amino acids, precedes a 169 as extracellular portion. Four putative N-glycosylation sites are present in the extracellular portion. Comparison of the cDNA coding for NKp80 in EMBL/GenBank/DDBJ databases revealed its identity with the recently described KLRF1 cDNA (9) the molecular product of which had not been identified.

Discussion

NKp80 is a 80 kD triggering surface molecule expressed by all human NK cells and by a small subset of T cells characterized by the CD3+ CD56+ surface phenotype.

Remarkably, NKp80 is involved in the NK-mediated cytolysis of PHA-induced lymphoblasts, but not of T cell leukemias and tumors of different histotypes.

NKp80 represents a novel marker for human NK cells. Although its expression largely overlaps with that of CD56 in freshly isolated peripheral blood lymphocytes (being expressed also by the infrequent CD3+ CD56+ T cells), different from CD56, NKp80 is not expressed by PHA-activated T cells.

The expression of NKp80 was also analyzed in a panel of 15 patients affected by LGL expansion. All CD3− LGL expansions expressed NKp80. Among the CD3+ LGL expansions analyzed, 6 out of 10 expressed NKp80, while CD16 and CD56 were expressed in 7/10 and 5/10 respectively. It results from these data that NKp80 may be used as an additional marker for typing LDGL and for identifying abnormal cells in the whole lymphocyte population of these patients.

The analysis of the expression of NKp80 in NK cell lymphomas and leukemias, together with the analysis of NKp80 expression during the in vitro NK cell maturation from CD34+ precursors appear to be valuable for defining at which stage of NK cell differentiation NKp80 is expressed.

Regarding the functional capability of NKp80, the levels of surface expression in different NK cell clones correlated with the ability of these clones to respond to anti-NKp80 engagement. For example, the infrequent NKp80$^{dull}$ clones did not respond. More importantly, a marked heterogeneity existed also among NKp80$^{bright}$ NK cell clones. In this case, the magnitude of cytolytic responses of clones to anti-NKp80 mAb correlated with their NKp46$^{bright}$ vs. NKp46$^{dull}$ phenotype. A similar correlation has recently been established for NK cell responses to anti-2B4 mAb. These studies led to the conclusion that 2B4 rather than as a true receptor, could function as a co-receptor in the induction of the NK cell-mediated cytotoxicity. Thus, NKp80 appear to function as a co-receptor, cooperating with NKp46 and other activating receptors. A common feature of the triggering NK cell receptors discovered so far (including CD16, NKp30, NKp44, NKp46 and NKG2D) is their ability to transduce activating signals via the association with signaling polypeptides including CD3-ζ, FcεRIγ, DAP12 or DAP10. The presence of opposite charged residues within the transmembrane regions of the receptors and of the signaling polypeptides is thought to be crucial for their association. On the contrary, 2B4 molecules that are functioning as co-receptors, do not contain charged residues in their transmembrane portion and do not associate to classical signaling polypeptides. Although not shown, immunoprecipitation experiments failed to demonstrate NKp80-association with signaling molecules such as CD3-ζ, FcεRIγ and DAP12. Moreover, NKp80 does not contain charged amino acids in the transmembrane portion.

The isolation of the NKp80-specific cDNA revealed its identity with the recently described KLRF-1 cDNA (9). KLRF-1 transcripts were detected in different cell types (including monocytes, promyelomonocytic and monocytic cell lines, the erythroblastoid K562 cell line and activated NK cells). In addition, according to the presence of Tyrosine-based moities in the predicted cytoplasmic portion, an inhibitory function was suggested for the putative encoded-molecule (9).

On the contrary, the expression of NKp80 molecule was confined to NK cells and to a minor CD3+ T cell subset, while other cell types including B cells (see FIG. 1), monocytes/macrophages or myelomonocytic cell lines (including U937, THP-1) and K562 were negative (not shown).

Moreover, NKp80 displayed an activating rather than an inhibitory function. It is possible that the Tyrosine-based motifs contained within the cytoplasmic portion of NKp80 (which do not belong to typical ITIM motifs) may serve to interact with still undefined cytoplasmic adaptor proteins involved in the transduction of activating signals. Although not shown, Tyrosine phosphorylation of NKp80 molecules has been detected upon treatment of NK cells with sodium pervanadate. Along this line, also 2B4 molecules contain Tyrosine-based motifs in the cytoplasmic portion. Following Tyrosine phosphorylation, 2B4 associates with a small cytoplasmic protein termed SH2D1A or SAP that plays a crucial role in the 2B4-mediated activating signals.

BIBLIOGRAPHIC REFERENCES

1. Sivori, S., M. Vitale, L. Morelli, L. Sanseverino, R. Augugliaro, C. Bottino, L. Moretta, and A. Moretta. p46, a novel Natural Killer cell-specific surface molecule which mediates cell activation. J. Exp. Med. 1997. 186: 1129-1136.
2. Vitale, M., C. Bottino, S. Sivori, L. Sanseverino, R. Castriconi, R. Marcenaro, R. Augugliaro, L. Moretta, and A. Moretta. NKp44, a novel triggering surface molecule specifically expressed by activated Natural Killer cells is involved in non-MHC restricted tumor cell lysis. J. Exp. Med. 1998. 187:2065-2072.
3. Pende, D., S. Parolini, A. Pessino, S. Sivori, R. Augugliaro, L. Morelli, E. Marcenaro, L. Accame, A. Malaspina, R. Biassoni, C. Bottino, L. Moretta, and A. Moretta. Identification and molecular characterization of NKp30, a novel triggering receptor involved in natural cytotoxicity mediated by human natural killer cells. J. Exp. Med. 1999. 190:1505-1516.
4. Ciccone, E., D. Pende, M. Vitale, L. Nanni, C. Di Donato, C. Bottino, L. Morelli, O. Viale, A. Amoroso, A. Moretta and Moretta L. Self Class I molecules protect normal cells from lysis mediated by autologous Natural Killer Cells. Eur. J. Immunol. 1994.24:1003-1006.
5. Bottino, C., G Tambussi, S Ferrini., E Ciccone., M. C. Mingari., P Varese., L Moretta., and A Moretta. Two subsets of human T lymphocytes expressing gamma/delta antigen receptor are identified by monoclonal antibodies directed to two distinct molecular forms of the receptor. J. Exp. Med. 1988.168:491-505.
6. Poggi, A., R. Pardi, N. Pella, L. Morelli, S. Sivori, M. Vitale, V. Revello, A. Moretta and L. Moretta. CD45-mediated regulation of LFA1 function in human natural killer cells. Anti-CD45 monoclonal antibodies inhibit the calcium mobilization induced via LFA1 molecules. Eur. J. Immunol. 1993. 23:2445-2463.
7. Semenzato, G., R. Zambello, G. Starkebaum, K. Oshimi and T. P. Lougharn Jr. The lymphoproliferative disease of granular lymphocytes: Updated criteria for diagnosis. Blood 1997. 89: 256-260.
8. Pessino, A., S. Sivori, C. Bottino, A. Malaspina, L. Morelli, L. Moretta, R. Biassoni, and A. Moretta. Molecular cloning of NKp46: a novel member of the immunoglobulin superfamily involved in triggering of natural cytotoxicity. J. Exp. Med. 1998. 188:953-960.
9. Roda-Navarro, P., I. Arce, M. Renedo, K. Montgomery, R. Kucherlapati, and E. Fernandez-Ruiz. Human KLRF1, a novel member of the killer cell lectin-like receptor gene family: molecular characterization, genomic structure, physical mapping to the NK gene complex and expression analysis. Eur. J. Immunol. 2000.30:568-576.

We claim:

1. A method of detecting the presence of NK cells in a sample comprising contacting said sample with a composition comprising a first antibody, or an immunoreactive fragment thereof, that binds to a polypeptide comprising ID NO: 1 (NKp80) under conditions that allow for the formation of an immune complex between the cells and said first antibody or said immunoreactive fragment thereof, contacting said sample with a second composition comprising an anti-CD3 antibody under conditions that allow for a second immune complex formation and detecting the CD3 negative and NKp80 positive cells to indicate the presence of NK cells in the sample.

2. A method of eliminating NK cells in a sample comprising contacting said sample with a composition comprising an antibody, or an immunoreactive fragment thereof, that binds to a polypeptide comprising ID NO: 1 (NKp80) under conditions that allow for the formation of an immune complex between the cells and said antibody, or said immunoreactive fragment thereof, and eliminating the immune complex formed by said antibody, or immunoreactive fragment thereof, and said cells.

3. A method of recovering NK cells in a sample comprising contacting said sample with a composition comprising an antibody, or an immunoreactive fragment thereof, that binds to a polypeptide comprising ID NO: 1 (NKp80) under conditions that allow for the formation of an immune complex between the cells and said antibody, or said immunoreactive fragment thereof, and recovering the immune complex formed by said antibody, or an immunoreactive fragment thereof, and said cells.

4. A method of stimulating NK cell cytotoxicity comprising contacting NK cells expressing a polypeptide comprising SEQ ID NO: 1 (NKp80) with a composition comprising an NKp80 specific antibody, or an immunoreactive fragment thereof, that binds to said NKp80 polypeptide, said NKp80 polypeptide having NK cell triggering activity, under conditions that allow for the formation of an immune complex between the cells and said antibody or said immunoreactive fragment thereof and stimulating NK cell cytotoxicity by crosslinking immune complex formed on the cell surface between said NKp80 specific antibody, or an immunoreactive fragment thereof, and said NKp80 polypeptide.

5. A method of inhibiting NK cell cytotoxity comprising contacting NK cells expressing a polypeptide comprising SEQ ID NO: 1 (NKp80) with a composition comprising an NKp80 masking antibody, or an immunoreactive fragment thereof, that binds said NKp80 polypeptide, said NKp80 polypeptide having NK cell triggering activity, under conditions that allow for the formation of an immune complex between the NK cells and said NKp80 masking antibody, or said immunoreactive fragment thereof, to block the interaction of NKp80 with its ligand.

* * * * *

SEQUENCE LISTING

<160> NUMBER OF SEQ ID NOS: 2

<210> SEQ ID NO 1
<211> LENGTH: 231
<212> TYPE: PRT
<213> ORGANISM: Homo sapiens

<400> SEQUENCE: 1

```
Met Gln Asp Glu Glu Arg Tyr Met Thr Leu Asn Val Gln Ser Lys Lys
1               5                   10                  15

Arg Ser Ser Ala Gln Thr Ser Cys Leu Thr Phe Lys Asp Tyr Ser Val
            20                  25                  30

Thr Leu His Trp Tyr Lys Ile Leu Leu Gly Ile Ser Gly Thr Val Asn
        35                  40                  45

Gly Ile Leu Thr Leu Thr Leu Ile Ser Leu Ile Leu Leu Val Ser Cys
    50                  55                  60

Gly Val Leu Leu Lys Cys Gln Lys Gly Ser Cys Ser Asn Ala Thr Gln
65                  70                  75                  80

Tyr Glu Asp Thr Gly Asp Leu Lys Val Asn Asn Gly Thr Arg Arg Asn
                85                  90                  95
```

Ile Ser Asn Lys Asp Leu Cys Ala Ser Arg Ser Ala Asp Gln Thr Val
              100                 105                 110

Leu Cys Gln Ser Glu Trp Leu Lys Tyr Gln Gly Lys Cys Tyr Trp Phe
          115                 120                 125

Ser Asn Glu Met Lys Ser Trp Ser Asp Ser Tyr Val Tyr Cys Leu Glu
      130                 135                 140

Arg Lys Ser His Leu Leu Ile Ile His Asp Gln Leu Glu Met Ala Phe
145                 150                 155                 160

Ile Gln Lys Asn Leu Arg Gln Leu Asn Tyr Val Trp Ile Gly Leu Asn
                  165                 170                 175

Phe Thr Ser Leu Lys Met Thr Trp Thr Trp Val Asp Gly Ser Pro Ile
              180                 185                 190

Asp Ser Lys Ile Phe Phe Ile Lys Gly Pro Ala Lys Glu Asn Ser Cys
          195                 200                 205

Ala Ala Ile Lys Glu Ser Lys Ile Phe Ser Glu Thr Cys Ser Ser Val
      210                 215                 220

Phe Lys Trp Ile Cys Gln Tyr
225                 230

<210> SEQ ID NO 2
<211> LENGTH: 1242
<212> TYPE: DNA
<213> ORGANISM: Homo sapiens

<400> SEQUENCE: 2

```
atttcatgtt atacttaata aaacaaaaca tacctgtata cacacacatt cactcacatt      60
gaagatgcaa gatgaagaaa gatacatgac attgaatgta cagtcaaaga aaaggagttc     120
tgcccaaaca tctcaactta catttaaaga ttattcagtg acgttgcact ggtataaaat     180
cttactggga acatctggaa ccgtgaatgg tattctcact ttgactttga tctccttgat     240
cctgttggtt tctcagggag tattgctaaa atgccaaaaa ggaagttgtt caaatgccac     300
tcagtatgag gacactggag atctaaaagt gaataatggc acaagaagaa atataagtaa     360
taaggacctt tgtgcttcga gatctgcaga ccagacagta ctatgccaat cagaatggct     420
caaataccaa gggaagtgtt attggttctc taatgagatg aaaagctgga gtgacagtta     480
tgtgtattgt ttggaaagaa aatctcatct actaatcata catgaccaac ttgaaatcgc     540
ttttatacag aaaaacctaa gacaattaaa ctacgtatgg attgggctta actttacctc     600
cttgaaaatg acatggactt gggtggatgg ttctccaata gattcaaaga tattcttcat     660
aaagggacca gctaaagaaa acagctgtgc tgccattaag gaaagcaaaa ttttctctga     720
aacctgcagc agtgtttttca aatggatttg tcagtattag agtttgacaa aattcacagt     780
gaaataatca atgatcacta ttttggcct attagtttct aatattaatc tccaggtgta     840
agattttaaa gtgcaattaa atgccaaaat ctcttctccc ttctccctcc atcatcgaca     900
ctggtctagc ctcagagtaa cccctgttaa caaactaaaa tgtacacttc aaaattttta     960
cgtgatagta taaccaatg tgacttcatg tgatcatatc caggattttt attcgtcgct    1020
tattttatgc caaatgtgat caaattatgc ctgttttct gtatcttgcg ttttaaattc    1080
ttaataaggt cctaaacaaa atttcttata tttctaatgg ttgaattata atgtgggttt    1140
atacattttt tacccttttg tcaaagagaa ttaactttgt ttccaggctt ttgctactct    1200
tcactcagct acaataaaca tcctgaatgt tttcttaaaa aa                       1242
```